United States Patent [19]

Bundy

[11] 4,176,282

[45] Nov. 27, 1979

[54] 2-DECARBOXY-2-ALKYLCARBONYL-3,7-INTER-M-PHENYLENE-3-OXA-4,5,6-TRINOR-PGF$_1$ COMPOUNDS

[75] Inventor: Gordon L. Bundy, Portage, Mich.

[73] Assignee: The Upjohn Company, Kalamazoo, Mich.

[21] Appl. No.: 925,262

[22] Filed: Jul. 17, 1978

Related U.S. Application Data

[62] Division of Ser. No. 888,695, Mar. 21, 1978, Pat. No. 4,123,463.

[51] Int. Cl.$^2$ ............................................. C07C 177/00
[52] U.S. Cl. ................................................. 260/590 C
[58] Field of Search ..................................... 260/590 C

[56] References Cited

U.S. PATENT DOCUMENTS

| | | | |
|---|---|---|---|
| 3,931,296 | 1/1976 | Hayashi et al. | 560/121 |
| 3,953,435 | 4/1976 | Hayashi et al. | 542/426 |
| 4,066,751 | 1/1978 | Hayashi et al. | 560/121 |

OTHER PUBLICATIONS

Derwent, CPI Farmdoc, 93049x/50 (Ja-044211).
Derwent Farmdoc, CPI No. 35953x.
Derwent Farmdoc, CPI No. 94924x.

*Primary Examiner*—Gerald A. Schwartz
*Attorney, Agent, or Firm*—Robert A. Armitage

[57] ABSTRACT

The present invention provides novel prostaglandin analogs wherein the C-2 carboxyl is replaced by alkylcarbonyl, i.e., a C-2 ketone. These novel 2-decarboxy-2-alkylcarbonyl-PG-type compounds are disclosed as improved gastrointestinal cytoprotective agents, being devoid or substantially devoid of other prostaglandin-type effects (e.g., smooth muscle or cardiovascular).

37 Claims, No Drawings

2-DECARBOXY-2-ALKYLCARBONYL-3,7-INTER-M-PHENYLENE-3-OXA-4,5,6-TRINOR-PGF$_1$ COMPOUNDS

The present application is a divisional application of Ser. No. 888,695, filed Mar. 21, 1978, now U.S. Pat. No. 4,123,463.

The present invention relates to prostaglandin analogs, for which the essential material constituting disclosure therefor is incorporated by reference here from Ser. No. U.S. Pat. No. 4,123,463.

I claim:

1. A prostaglandin analog of the formula

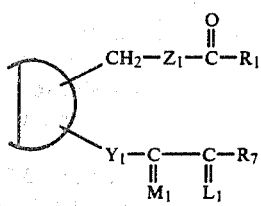

wherein D is

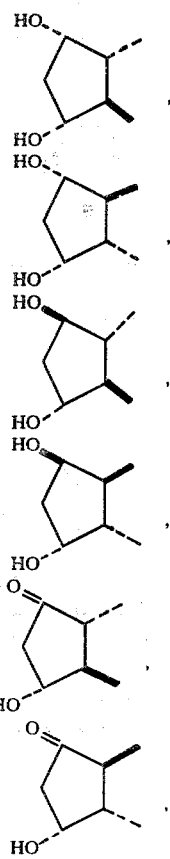

wherein $R_1$ is alkyl of one to 4 carbon atoms, inclusive; wherein $L_1$ is

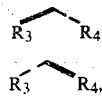

or a mixture of

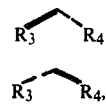

wherein $R_3$ and $R_4$ are hydrogen, methyl, or fluoro, being the same or different, with the proviso that one of $R_3$ and $R_4$ is methyl only when the other is hydrogen or methyl;

wherein $M_1$ is

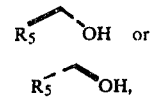

wherein
$R_5$ is hydrogen or methyl;
wherein $R_7$ is
(1) $-(CH_2)_m-CH_3-$,

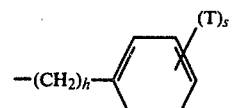

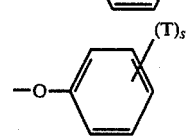

wherein h is zero to three, inclusive, wherein m is one to 5, inclusive, s is zero, one, 2, or 3 and T is chloro, fluoro, trifluoromethyl, alkyl of one to 3 carbon atoms or alkoxy of one to 3 carbon atoms, the various T's being the same or different, with the proviso that not more than two T's are other than alkyl;

wherein $Y_1$ is
(1) trans—CH=CH—,
(2) cis—CH=CH—,
(3) —CH$_2$CH$_2$—, or
(4) —C≡C—; and
wherein $Z_1$ is

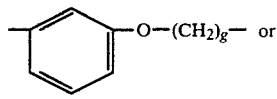

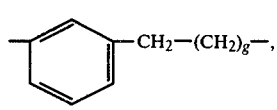

wherein g is one, two, or three.

2. A prostaglandin analog according to claim 1, wherein $R_1$ is methyl.

3. A prostaglandin analog according to claim 2, wherein D is

D is 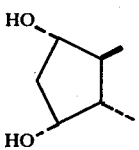

4. 2-Decarboxy-2-methylcarbonyl-3,7-inter-m-phenylene-3-oxa-4,5,6-trinor-8β,12α-PGF₁α, a prostaglandin analog according to claim 3.

5. A prostaglandin analog according to claim 2, wherein D is

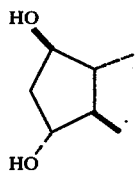

6. 2-Decarboxy-2-methylcarbonyl-3,7-inter-m-phenylene-3-oxa-4,5,6-trinor-PGF₁β, a prostaglandin analog accoridng to claim 5.

7. A prostaglandin analog according to claim 5, wherein D is

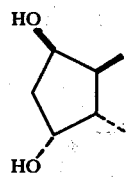

8. 2-Decarboxy-2-methylcarbonyl-3,7-inter-m-phenylene-3-oxa-4,5,6-trinor-8β, 12α-PGF₂β, a prostaglandin analog according to claim 7.

9. A prostaglandin analog according to claim 2, wherein D is

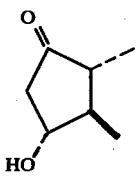

10. 2-Decarboxy-2-methylcarbonyl-3,7-inter-m-phenylene-3-oxa-4,5,6-trinor-PGE₁, a prostaglandin analog according to claim 9.

11. A protaglandin analog according to claim 2, wherein D is

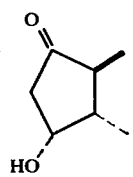

12. 2-Decarboxy-2-methylcarbonyl-3,7-inter-m-phenylene-3-oxa-4,5,6-trinor-8β, 12α-PGE₁, a prostaglandin analog according to claim 11.

13. A prostaglandin analog according to claim 2, wherein D is

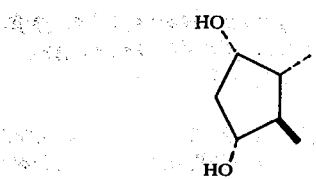

14. A prostaglandin analog according to claim 13, wherein $Y_1$ is cis—CH=CH—.

15. 2-Decarboxy-2-methylcarbonyl-3,7-inter-m-phenylene-3-oxa-4,5,6-trinor-13-cis-PGF₁α, a prostaglandin analog according to claim 14.

16. A prostaglandin analog according to claim 13, wherein $Y_1$ is —CH₂CH₂—.

17. 2-Decarboxy-2-methylcarbonyl-3,7-inter-m-phenylene-3-oxa-4,5,6-trinor-13,14-dihydro PGF₁α, a prostaglandin analog according to claim 16.

18. A prostaglandin analog according to claim 13, wherein $Y_1$ is —C≡C—.

19. 2-Decarboxy-2-methylcarbonyl-3,7-inter-m-phenylene-3-oxa-4,5,6-trinor-13,14-didehydro-PGF₁α, a prostaglandin analog according to claim 18.

20. A prostaglandin analog according to claim 13, wherein $Y_1$ is trans—CH=CH—.

21. A prostaglandin analog according to claim 20, wherein $R_7$ is

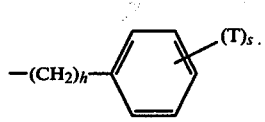

22. 2-Decarboxy-2-methylcarbonyl-3,7-inter-m-phenylene-3-oxa-4,5,6-18,19,20-hexanor-17-phenyl-PGF₁α, a prostaglandin analog according to claim 21.

23. prostaglandin analog according to claim 20, wherein $R_7$ is

24. 2-Decarboxy-2-methylcarbonyl-3,7-inter-m-phenylene-3-oxa-4,5,6-17,18,19,20-heptanor-16-phenoxy-PGF₁α, a prostaglandin analog according to claim 23.

25. A prostaglandin analog according to claim 20, wherein $R_7$ is —(CH₂)$_m$—CH₃—.

26. A prostaglandin analog according to claim 25, wherein $Z_1$ is

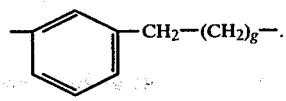

27. 2-Decarboxy-2-methylcarbonyl-3,7-inter-m-phenylene-4,5,6-trinor-PGF₁α, a prostaglandin analog according to claim 26.

28. A prostaglandin analog according to claim 25, wherein $Z_1$ is

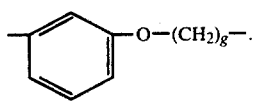

29. A prostaglandin analog according to claim 25, wherein $R_5$ is methyl.

30. 2-Decarboxy-2-methylcarbonyl-3,7-inter-m-phenylene-3-oxa-4,5,6-trinor-15-methyl-PGF$_1\alpha$, a prostaglandin analog according to claim 25.

31. A prostaglandin analog according to claim 25, wherein $R_5$ is hydrogen.

32. A prostaglandin analog according to claim 31, wherein one of $R_3$ and $R_4$ is fluoro.

33. 2-Decarboxy-2-methylcarbonyl-3,7-inter-m-phenylene-3-oxa-4,5,6-trinor-16,16-difluoro-PGF$_1\alpha$, a prostaglandin analog according to claim 32.

34. A prostaglandin analog according to claim 31, wherein at least one of $R_3$ and $R_4$ is methyl.

35. 2-Decarboxy-2-methylcarbonyl-3,7-inter-m-phenylene-3-oxa-4,5,6-trinor-16,16-dimethyl-PGF$_1\alpha$, a prostaglandin analog according to claim 34.

36. A prostaglandin analog according to claim 31, wherein $R_3$ and $R_4$ are both hydrogen.

37. 2-Decarboxy-2-methylcarbonyl-3,7-inter-m-phenylene-3-oxa-4,5,6-trinor-PGF$_1\alpha$, a prostaglandin analog according to claim 36.

* * * * *